United States Patent [19]

Tsuboi et al.

[11] Patent Number: 5,196,442
[45] Date of Patent: Mar. 23, 1993

[54] FORMICIDAL AGENT FOR COMBATING TERMITES

[75] Inventors: Sinichi Tsuboi; Ikuro Honda; Sakae Murata; Yumi Hattori, all of Tokyo, Japan

[73] Assignee: Nihon Tokushu Noyaku Seizo K.K., Tokyo, Japan

[21] Appl. No.: 770,682

[22] Filed: Oct. 3, 1991

Related U.S. Application Data

[62] Division of Ser. No. 537,405, Jun. 13, 1990, Pat. No. 5,087,632.

[30] Foreign Application Priority Data

Jun. 16, 1989 [JP] Japan .................... 1-52243
Feb. 28, 1990 [JP] Japan .................... 2-45720

[51] Int. Cl.$^5$ .............................................. A01N 43/40
[52] U.S. Cl. ............................................... 514/357
[58] Field of Search ................................... 514/357

[56] References Cited

U.S. PATENT DOCUMENTS 4,963,574 10/1990 Bachmann et al. ............. 514/357
5,063,236 11/1991 Gsell .................................. 514/357

*Primary Examiner*—Allen J. Robinson
*Attorney, Agent, or Firm*—Sprung Horn Kramer & Woods

[57] ABSTRACT

A method of combating termites comprising combating termites and/or their habit with an effective termite combating amount of at least one active compound of the formula (I)

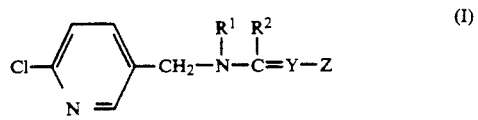

wherein
$R^1$ represents hydrogen atom or a $C_{1-4}$ alkyl group,
$R^2$ represents —S—$CH_3$ or

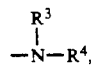

wherein $R^3$ and $R^4$ each represent hydrogen atom or a $C_{1-4}$ alkyl group,
Y represents CH or N, and
Z represents a nitro group or a cyano group, provided that where Z represents a cyano group, then Y represents N, either alone or in admixture with an extender and/or a surface active agent.

12 Claims, No Drawings

FORMICIDAL AGENT FOR COMBATING TERMITES

This is a division of application Ser. No. 537,405, filed Jun. 13, 1990 U.S. Pat. No. 5,087,632.

The present invention relates to the use of known nitromethylene-, nitroimino- and cyanoimino- compounds as formicidal agents for combating termites.

The nitromethylene-, nitroimino- and cyanoimino- compounds have already been known and the use thereof as insecticides has also been known. (Japanese Patent application 264020/1988, Japanese Patent application 299419/1988 and EP-A 302389)

There has not been known any formicidal activity of said compounds up to now.

Termites are known as one of the most familiar pests infesting wood and lumber so that due to serious damages caused thereby on wooden buildings and the like, undesirable effects on living environment and cultural assets principally made of wooden material have posed a social problem, urgently requiring effective controlling of the pests.

In recent years, Chlordane, extensively used heretofore as formicidal agent for killing termites in this country was prohibited to use due to its long-lasting residual effect and the resulting environmental pollution, while instead thereof use has been made, at present, of organophosphorus insecticides such as phoxime [O-(α-cyanobenzylideneamino)O,O-diethylphosphorothioate], chlorpyriphos [0,0-diethyl-3,5,6-trichloro-2-pyridyl-phosphorothioate], etc., as well as pyrethroides series insecticides such as permethrin [5-benzyl-3-furylmethyl-3-(2-methoxy-carbonyl-1-propenyl)-2,2-dimethylcyclopropane carboxylate], decamethrin [α-cyano-3-phenoxybenzyl d,l-cis-3-(2,2-dibromovinyl)-2,2-dimethyl cyclopropane carboxylate], etc.

However, even the above-mentioned insecticides are unsatisfactory as far as effective concentration and safety for human health are concerned.

Furthermore, in view of the nature of houses and cultural assets made from wooden material, treatment with formicidal agent thereon was naturally limited in the number of applications.

It has been found that the known compounds of the formula (I)

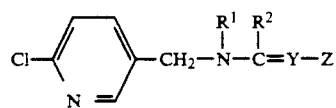

wherein
$R^1$ represents hydrogen atom or a $C_{1-4}$ alkyl group,
$R^2$ represents —S—$CH_3$ or

wherein $R^3$ and $R^4$ each represent hydrogen atom or $C_{1-4}$ alkyl group,
Y represents CH or N, and
Z represents a nitro group or a cyano group, provided that where Z represents a cyano group, then Y represents N,
exhibit powerful formicidal properties on termites.

Surprisingly, the compounds according to the invention, of the formula (I) exhibit an extremely strong formicidal action on termites and the function is substantially superior to that of known formicidal agents for termites, and in view of the fact that the formicidal concentration of the active compounds is extremely lower than that of known formicidal agents, the compounds of the formula (I) are acceptable in an environmental aspect too. Furthermore, the compounds of the formula (I) also exhibit residual activities on termites at a lower concentration than known agents, the compounds of the formula (I) besides controlling termites safely and precisely, can also advantageously be used for wooden buildings which are easily damaged by termites.

In the formula (I),
$R^1$ preferably represents hydrogen, methyl, ethyl or n-propyl,
$R^2$ represents —S—$CH_3$ or

wherein $R^3$ and $R^4$ each represent hydrogen atom, methyl or ethyl,
Y represents CH or N, and
Z represents nitro group or cyano group, provided that Z represents cyano group, Y represents N.

As examples of the active substances according to the invention there may be mentioned:

1-(2-chloro-5-pyridylmethylamino)-1-methylamino-2-nitroethylene,
1-[N-(2-chloro-5-pyridylmethyl)-N-methylamino]-1-methylamino-2-nitroethylene,
1-amino-1-[N-(2-chloro-5-pyridylmethyl)-N-methylamino]-2-nitroethylene,
3-(2-chloro-5-pyridylmethyl)-3-methyl-2-nitroguanidine,
1-(2-chloro-5-pyridylmethyl)-3-cyano-2-methylisothiourea,
1-(2-chloro-5-pyridylmethylamino)-1-methylamino-2-nitroethylene,
3-(2-chloro-5-pyridylmethyl)-1-methyl-2-nitroguanidine,
1-(2-chloro-5-pyridylmethyl)-1-dimethylamino-2-nitroethylene,
1-[N-(2-chloro-5-pyridylmethyl)-N-methylamino]-1-dimethylamino-2-nitroethylene,
3-(2-chloro-5-pyridylmethyl)-1,1-dimethyl-2-nitroguanidine,
3-(2-chloro-5-pyridylmethyl)-1,3-dimethyl-2-nitroguanidine,
1-amino-1-[N-(2-chloro-5-pyridylmethyl)-N-ethylamino]-2-nitroethylene,
1-[N-(2-chloro-5-pyridylmethyl)-N-ethylamino]-1-methylamino-2-nitroethylene,
1-[N-(2-chloro-5-pyridylmethyl)-N-n-propylamino]-1-methylamino-2-nitroethylene,
1-[N-(2-chloro-5-pyridylmethyl)-N-ethylamino]-1-ethylamino-2-nitroethylene, and
3-(2-chloro-5-pyridylmethyl)-3-ethyl-1-methyl-2-nitroguanidine.

The active substances to be used according to the invention exhibit powerful formicidal effects against termites. They can therefore be used as formicidal agent for combating termites.

As individual examples of termites to be controlled by the formicidal agent according to the present invention the following ones can be mentioned:

From the order of Isoptera: *Deucotermes speratus, Coptotermes formosanus, Glyptotermes fuscus, Glyptotermes satsumensis, Glyptotermes nakajimai, Glyptotermes kodamai, Incisitermes minor, Neotermes koshunensis, Cryptotermes domesticus, Hodotermopsis japonica, Reticulitermes miyatakei, Odontotermes formosanus, Nasutitermus takasagoensis,* and *Capritermes nitobei.*

The active compounds of the general formula (I) in the present invention can be prepared into the customary formulations, such as solutions, emulsions, suspensions, powders, foams, pastes, granules, aerosols, natural and synthetic materials impregnated with active compounds, and micro-capsules.

These formulations can be produced in a known manner, for example, by mixing the active compounds with extenders, that is to say liquid or liquefied gaseous or solid diluents or carriers, optionally with the use of surface-active agents, that is to say emulsifying agents, dispersing agents, and/or foam-forming agents. In the case of using water as an extender, organic solvents can, for example, also be used as auxiliary solvents.

As liquid diluents or carriers can be mentioned, for example, aromatic hydrocarbons, such as xylene, toluene and alkyl naphthalenes, chlorinated aromatic or chlorinated aliphatic hydrocarbons, such as, chlorobenzenes, chloroethylenes and methylene chloride, aliphatic or alicyclic hydrocarbons, such as cyclohexane or paraffins, for example, mineral oil fractions, alcohols, such as butanol or glycol, as well as their ethers and esters, ketones, such as acetone, methyl ethyl ketone, methyl isobutyl ketone or cyclohexanone, or strongly polar solvents, such as dimethylformamide and dimethylsulfoxide, as well as water.

By liquefied gaseous diluents or carriers liquids are meant which are gaseous at normal temperature and under normal pressure, for example, aerosol propellants, such as halogenated hydrocarbons, as well as butane, propane, nitrogen and carbon dioxide.

As solid diluents there may be used ground natural minerals, such as kaolins, clays, talc, chalk, quartz, attapulgite, montmorillonite or diatomaceus earth, and ground synthetic minerals, such as highly-dispersed silicic acid, alumina and silicates.

As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used nonionic and anionic emulsifiers, such as polyoxyethylene-fatty acid esters, polyoxyethylene-fatty alcohol ethers, for example, alkylaryl polyglycol ethers, alkylsulfonates, alkylsulfates, arylsulfonates as well as albumin hydrolysis products. Dispersing agents include, for example, lignin sulfite waste liquors and methyl cellulose.

Adhesives such as carboxymethyl cellulose and natural and synthetic polymers (such as gum arabic, polyvinyl alcohol and polyvinyl acetate) can be used in the formulations in the form of powders, granules or emulsifiable concentrations.

It is possible to use colorants such as inorganic pigments, for example, iron oxide, titanium oxide and Prussian Blue and organic dyestuffs, such as alizarin dyestuffs, azo dyestuffs or metal phthalocyanine dyestuffs, and trace elements, such as salts of iron, manganese, boron, copper, cobalt, molybdenum and zinc.

The formulations, in general, contain from 0.1 to 95 percent by weight of active compound, preferably from 0.5 to 90 percent by weight.

Furthermore, the active compound of the present invention having the formula (I) can be present as a mixture with a synergist in a formulation or a use form, of a type that is commercially useful. The term "synergist" denotes a compound which is not active in itself, but promotes the action of an active compound. The content of the active compounds having the general formula (I) of the present invention in commercially useful formulations can vary within a wide range. The active compound concentration of the use forms can be from 0.0000001 to 100 percent by weight, preferably from 0.0001 to 1 percent by weight.

The compounds of the formula (I) may be employed in a customary manner appropriate for a particular use form.

The content of the present invention will be concretely explained by way of the following examples but the present invention should not be limited only thereto.

Biotest:

Compounds under test

Examples of the active compounds according to the present invention:

I.1  1-(2-chloro-5-pyridylmethylamino)-1-methylamino-2-nitroethylene.

I.2  1-[N-(2-chloro-5-pyridylmethyl)-N-methylamino]-1-methylamino-2-nitroethylene, I.3  1-amino-1-[N-(2-chloro-5-pyridylmethyl)-N-methylamino]-2-nitroethylene, I.4  1-(2-chloro-5-pyridylmethyl)-3-cyano-2-methylisothiourea, I.5  3-(2-chloro-5-pyridylmethyl)-3-methyl-2-nitroguanidine, I.6  1-amino-1-[N-(2-chloro-5-pyridylmethyl)-N-ethylamino]-2-nitroethylene I.7  1-[N-(2-chloro-5-pyridylmethyl)-N-ethylamino]-1-methylamino-2-nitroethylene I.8  1-[N-(2-chloro-5-pyridylmethyl)-N-ethylamino]-1-ethylamino-2-nitroethylene I.9  3-(2-chloro-5-pyridylmethyl)-3-ethyl-1-methyl-2-nitroguanidine Comparative compounds:

A: permethrin

B: chlorpyriphos

EXAMPLE 1

Formicidal Test

Preparation of test formulation:

Solvent: 3 parts by weight of dimethyl formamide

Emulsifier: 1 part by weight of polyoxyethylene-alkylphenyl-ether

To prepare a suitable formulation of the active compound, 1 part by weight of each of the active compounds was mixed with the above-mentioned amount of the solvent containing the above-mentioned amount of the emulsifier, and the mixture was diluted with water to a predetermined concentration.

Test method:

1 ml of the aqueous solution prepared in the above-mentioned procedure was uniformly applied using a pipette onto a filter paper that was placed in a petri dish of 9 cm diameter. Ten head of worker termites *(Cop-* totermes formosanus) were released into the petri dish and it was kept in a constant temperature chamber at 25° C.

After four days, the mortality of the termites was investigated. This test procedure was carried out in duplicate per each concentration of the active comopounds under test.

The test results are shown in Table 1.

TABLE 1

| Compound | Concentration of active compound (ppm) | Mortality of termites after four days (%) |
|---|---|---|
| I.1 | 40 | 100 |
|  | 8 | 100 |
|  | 1.6 | 100 |
|  | 0.32 | 100 |
| I.2 | 40 | 100 |
|  | 8 | 100 |
|  | 1.6 | 100 |
|  | 0.32 | 100 |
| I.3 | 40 | 100 |
|  | 8 | 100 |
|  | 1.6 | 100 |
|  | 0.32 | 100 |
| I.4 | 40 | 100 |
|  | 8 | 100 |
|  | 1.6 | 100 |
|  | 0.32 | 100 |
| I.5 | 40 | 100 |
|  | 8 | 100 |
|  | 1.6 | 100 |
|  | 0.32 | 100 |
| I.6 | 40 | 100 |
|  | 8 | 100 |
|  | 1.6 | 100 |
|  | 0.32 | 100 |
| I.7 | 40 | 100 |
|  | 8 | 100 |
|  | 1.6 | 100 |
|  | 0.32 | 100 |
| I.8 | 40 | 100 |
|  | 8 | 100 |
|  | 1.6 | 100 |
|  | 0.32 | 100 |
| I.9 | 40 | 100 |
|  | 8 | 100 |
|  | 1.6 | 100 |
|  | 0.32 | 100 |
| A(permethrin) | 40 | 100 |
|  | 8 | 10 |
|  | 1.6 | 5 |
|  | 0.32 | 0 |
| B(chlorpyriphos) | 40 | 100 |
|  | 8 | 100 |
|  | 1.6 | 100 |
|  | 0.32 | 100 |
| Untreated |  | 0 |

EXAMPLE 2

Test on Residual Effect

Small sapwood blocks of Japanese redpine tree (2 cm×2 cm×2 cm) were soaked for one minute into the aqueous solution prepared by the similar procedure to Example 1.

After air-dried, they were kept in a constant temperature chamber at 40° C. for four weeks. Then each of the thus treated blocks was placed in a polymeric cup (10 cm diameter) containing 150 ml of sandy loam of 20% moisture content. Into each of the polymeric cups, 100 head of worker termites and 10 head of soldier termites (Coptotermes formosanus) were released. After three weeks, the degree of xylophagous damage in the block and the mortality of the termites were investigated.

Three tests were carried out in duplicate 25° C., and the results are shown in Table 2.

The index of xylophagous damage observed on the test blocks:

0: No damage 0.5: One to two traces of damage each having a depth of about 1 mm from the block surface 1: One to two evident damages each having a depth from 1 to 2 mm from the block surface 2: More than three evident damages or more than one deep trace of damage having a depth of more than 2 mm from the block surface 3: More than three deep damages 4: Evidently damaged zone covering up to about one third of the whole surface area of the block 5: Evidently damaged zone covering more than one third of the whole surface area of the block

TABLE 2

| Compound | Concentration of active compound (ppm) | Mortality termites after three weeks (%) | Degree of xylophagous damage in the pine tree block (0–5) |
|---|---|---|---|
| I.1 | 40 | 100 | 0 |
|  | 8 | 100 | 0 |
|  | 1.6 | 100 | 0 |
|  | 0.32 | 100 | 0 |
| I.2 | 40 | 100 | 0 |
|  | 8 | 100 | 0 |
|  | 1.6 | 100 | 0 |
|  | 0.32 | 100 | 0 |
| I.3 | 40 | 100 | 0 |
|  | 8 | 100 | 0 |
|  | 1.6 | 100 | 0 |
|  | 0.32 | 98 | 0 |
| I.4 | 40 | 100 | 0 |
|  | 8 | 100 | 0 |
|  | 1.6 | 98 | 0.5 |
|  | 0.32 | 72 | 1 |
| I.5 | 40 | 100 | 0 |
|  | 8 | 100 | 0 |
|  | 1.6 | 100 | 0 |
|  | 0.32 | 100 | 0 |
| I.6 | 40 | 100 | 0 |
|  | 8 | 100 | 0 |
|  | 1.6 | 100 | 0 |
|  | 0.32 | 100 | 0 |
| I.7 | 40 | 100 | 0 |
|  | 8 | 100 | 0 |
|  | 1.6 | 100 | 0 |
|  | 0.32 | 100 | 0 |
| I.8 | 40 | 100 | 0 |
|  | 8 | 100 | 0 |
|  | 1.6 | 100 | 0 |
|  | 0.32 | 100 | 0 |
| I.9 | 40 | 100 | 0 |
|  | 8 | 100 | 0 |
|  | 1.6 | 100 | 0 |
|  | 0.32 | 100 | 0 |
| A(permethrin) | 40 | 83 | 1 |
|  | 8 | 0 | 3 |
|  | 1.6 | 0 | 5 |
|  | 0.32 | 0 | 5 |
| B(chlorpyriphos)- | 40 | 100 | 0 |
|  | 8 | 67 | 1 |
|  | 1.6 | 8 | 2 |
|  | 0.32 | 0 | 5 |
| Untreated |  | 0 | 5 |

It will be appreciated that the instant specification is set forth by way of illustration and not limitation, and that various modifications and changes may be made without departing from the spirit and scope of the present invention.

What is claimed is:

1. A method of combating termites comprising contacting termites or their habitat with an effective termite combating amount of at least one active compound of the formula (I)

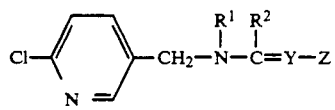

wherein
$R^1$ represents hydrogen atom or $C_{1-4}$ alkyl group,
$R^2$ represents —S—$CH_3$ or

wherein $R^3$ and $R^4$ each represent hydrogen atoms or a $C_{1-4}$ alkyl group,
Y represents N, and
Z represents a cyano group,
either alone or in admixture with an extender, a surface active agent or both.

2. A method according to claim 1, wherein $R^1$ is hydrogen, methyl, ethyl or n-propyl, $R^2$ is —S—$CH_3$ or

wherein $R^3$ and $R^4$ each represent hydrogen, methyl or ethyl, and
Z represents a cyano group.

3. A method according to claim 1, wherein the active compound is 1-(2-chloro-5-pyridylmethyl)-3-cyano-2-methylisothiourea.

4. A method according to claim 1, wherein the termites combatted are selected from the group consisting of *Deucotermes speratus, Coptotermes formosanus, Glyptotermes fuscus, Glyptotermes satsumensis, Glyptotermes nakajimai, Glyptotermes kodamai, Incisitermes minor, Neotermes koshunensis, Cryptotermes domesticus, Hodotermopsis japonica, Reticulitermes miyatakei, Odontotermes formosanus, Nasutitermus takasagoensis,* and *Capritermes nitobei.*

5. A method according to claim 1, wherein the extender is a liquid or solid diluent.

6. A method according to claim 1, wherein the surface active agent is selected from the group consisting of emulsifying agents, dispersing agents, foam-forming agents and mixtures thereof.

7. A method according to claim 1, wherein the extender is water or an organic solvent.

8. A method according to claim 1, wherein the extender is selected from the group consisting of an aromatic hydrocarbon, a chlorinated aromatic hydrocarbon, a chlorinated aliphatic hydrocarbon, an aliphatic hydrocarbon, an alicyclic hydrocarbon, a paraffin, an alcohol, a ketone and other strongly polar solvents.

9. A method according to claim 1, wherein the active compound is present in a formulation containing 0.1 to 95% by weight of the active compound.

10. A method according to claim 1, wherein the active compound is present in a formulation containing 0.5 to 90% by weight of the active compound.

11. A method according to claim 1, wherein the active compound is present in a formulation and the active compound concentration of the formulation is 0.0000001 to 100 percent by weight.

12. A method according to claim 1, wherein the active compound is present in a formulation and the active compound concentration of the formulation is 0.0001 to 1 percent by weight.

* * * * *

UNITED STATES PATENT AND TRADEMARK OFFICE
CERTIFICATE OF CORRECTION

PATENT NO. : 5,196,442

DATED : March 23, 1993

INVENTOR(S) : Tsuboi, et al.

It is certified that error appears in the above-identified patent and that said Letters Patent is hereby corrected as shown below:

Title Page    [30] Foreign Application Priority Data: After
" Jun. 16, 1989 [JP] Japan.... " delete
" 1-52243 " and substitute -- 1-152243 --

Signed and Sealed this

Twenty-third Day of August, 1994

Attest:

BRUCE LEHMAN

*Attesting Officer*     *Commissioner of Patents and Trademarks*